(12) United States Patent
Donnerhack et al.

(10) Patent No.: US 6,236,041 B1
(45) Date of Patent: May 22, 2001

(54) ANALYTICAL CONFIGURATION FOR MONITORING XENON-CONTAINING ANAESTHETIC GAS

(75) Inventors: Andreas Donnerhack, Krefeld; Ralf Igelhorst, Tönisvorst; Peter Neu, Mülheim; Renate Schmidt, Duisburg, all of (DE)

(73) Assignee: Messer Griesheim GmbH (DE)

( * ) Notice: Subject to any disclaimer, the term of this patent is extended or adjusted under 35 U.S.C. 154(b) by 0 days.

(21) Appl. No.: 09/077,771

(22) PCT Filed: Nov. 16, 1996

(86) PCT No.: PCT/EP96/05047

§ 371 Date: Jun. 1, 1998

§ 102(e) Date: Jun. 1, 1998

(87) PCT Pub. No.: WO97/20591

PCT Pub. Date: Jun. 12, 1997

(30) Foreign Application Priority Data

Jun. 12, 1995 (DE) .............................................. 195 45 598

(51) Int. Cl.[7] .................................................. B01D 59/44
(52) U.S. Cl. .............................................................. 250/281
(58) Field of Search .................................... 250/281, 282, 250/288

(56) References Cited

U.S. PATENT DOCUMENTS

| | | | |
|---|---|---|---|
| 4,810,877 | | 3/1989 | Holme ................................... 250/288 |
| 4,966,141 | * | 10/1990 | Bacaner et al. ................. 128/207.14 |
| 5,471,058 | * | 11/1995 | Nakagawa et al. ................... 250/282 |
| 5,528,923 | * | 6/1996 | Ledez et al. ......................... 73/19.12 |
| 6,076,392 | * | 6/2000 | Drzewiecki ........................... 73/23.2 |

* cited by examiner

*Primary Examiner*—Kiet T. Nguyen
(74) *Attorney, Agent, or Firm*—Connolly Bove Lodge & Hutz LLP

(57) ABSTRACT

An anesthesia system has ventilation gas supply flow structure for supplying ventilation gas to a patient. Structure is provided for the exhaled gas and for recycling the anesthetic gas-containing gas. The system uses a mass spectrometer connected to these flow structures to measure the content of at least one gas component in the gases and to control the flow through at least one of the flow structures in accordance with at least one measured value of the gas content.

17 Claims, 1 Drawing Sheet

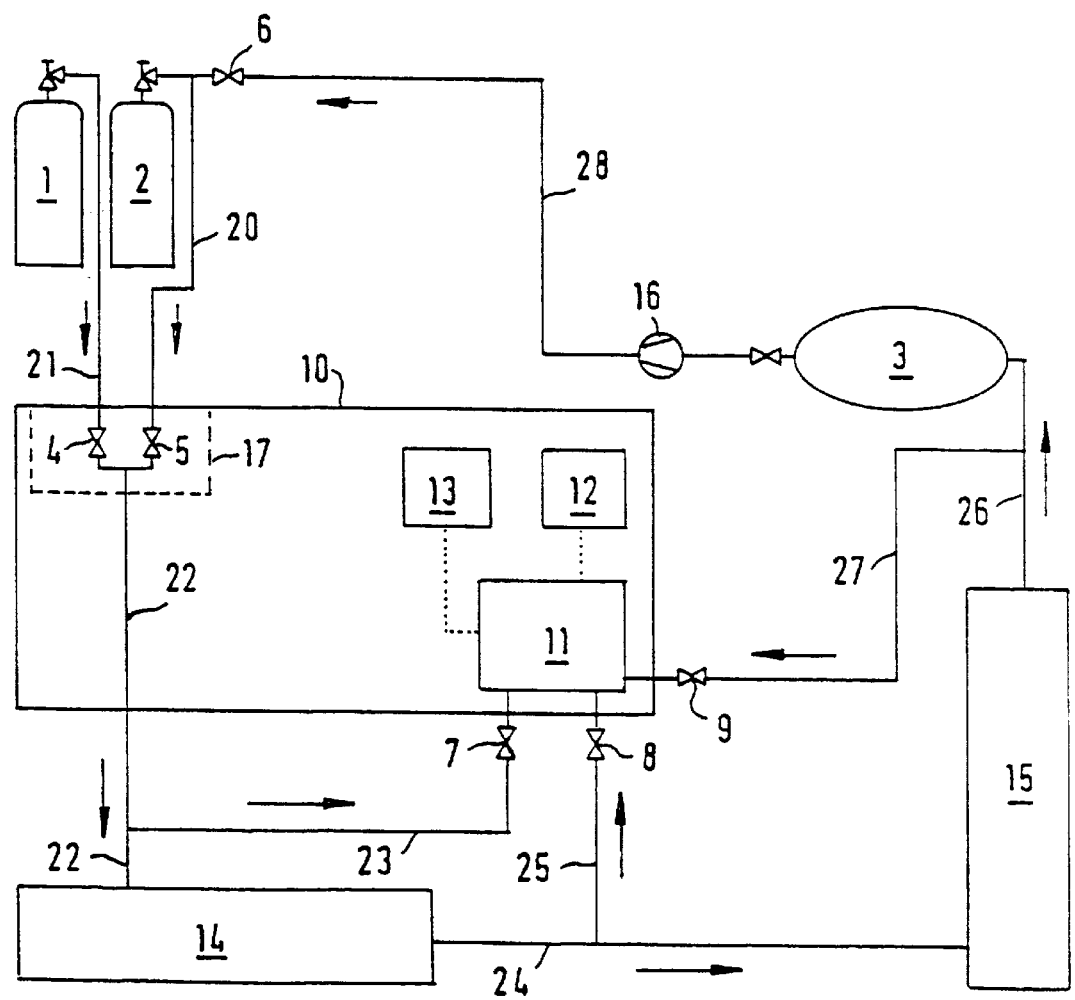

ANALYTICAL CONFIGURATION FOR MONITORING XENON-CONTAINING ANAESTHETIC GAS

BACKGROUND OF THE INVENTION

Anesthesia with xenon as an anesthetic gas has been described in the specialist medical literature for many years now. There are a number of medical advantages compared with laughing gas ($N_2O$) which is customary nowadays. However, the widespread introduction of xenon for this application has hitherto been impeded by the very much higher materials costs.

Developments in recent years have drastically reduced this difference in costs. These include improved anesthetic methods with low gas consumption (low-flow technique; minimal-flow technique) and methods for recovering the exhaled xenon mixture which make it possible to recycle the active component xenon in the anesthetic gas circulation (DE 44 11 533 C1).

Hitherto, admixture of anesthetic gas components has taken place manually.

DE 37 12 598 A1 describes an inhalation anesthetic machine. Besides other anesthetic gases xenon is mentioned as anesthetic gas. The machine has a gas analyzer, which is not characterized in detail.

DE 36 35 004 A1 describes a mass spectrometer for monitoring respiratory gases, the mass spectrometer measuring the carbon dioxide level.

Analytical determination of the anesthetic gas xenon is difficult as it is an inert gas. Gas analyzers customary in anesthetic machines are unsuitable for quantitative determination of xenon.

When xenon is used as anesthetic gas it is indispensable to recycle xenon from the exhaled gas for cost reasons. When xenon is recycled into the ventilation gas (inspiration side), satisfactory and reliable measurements of the gas mixture composition in the inspiration branch is indispensable. On the one hand, the gas mixture composition delivered from the recovery must be monitored continuously so that it is possible permanently to ensure the gas quality on recycling into the breathing circulation, and to switch over immediately to an auxiliary supply (for example gas cylinder) in the event of faults in the machine. On the other hand, the composition of the anesthetic gas in the breathing circulation must be continuously followed so that the clinician can monitor and control the progress of anesthesia individually. Besides the active component xenon and the respiratory component oxygen, it is additionally necessary to monitor the nitrogen content which is included as medically acceptable residual impurity from the recovery and whose accumulation in the breathing circulation must be limited. Besides reliable monitoring of the gas composition of inspired gas (gas for inhalation) and expired gas (gas exhaled by the patient), it is an object of the invention to automate the mixing of the respiratory gas components and the admixing of recycled anesthetic gas.

The invention now relates to an anesthesia system with mass spectrometer for quantitative measurement of at least one gas component in the ventilation gas, exhaled gas or recycled anesthetic gas-containing gas.

Mass spectrometers can in general be connected via a membrane or capillary to a gas stream to be analyzed. Coupling via a membrane has the disadvantage of a large gas consumption (for example around 5 1/h). Coupling capillaries is advantageous. The loss of gas can be reduced to about 0.5 1/h in this way. The capillary can consist of plastic, metal or glass. Metal capillaries are preferred, especially with prolonged measurement periods and lengthy capillaries. The capillaries may be employed, for example, with a length of from 6 to 10 meters. This permits flexibility in the site for setting up the mass spectrometer.

The mass spectrometer in the anesthesia system according to the invention is preferably used for simultaneous quantitative measurement of the gas components oxygen, anesthetic gas (for example xenon) and nitrogen in the inspired gas, expired gas or recycled anesthetic gas-containing gas. The measurement can be extended to other gas components such as carbon dioxide.

The anesthesia system is advantageously designed so that the mass spectrometer is connected via control valves to the gas lines for inspired gas, expired gas and, where appropriate, recovered anesthetic gas or recycled respiratory gas.

The anesthesia system contains at least one mass spectrometer which can be integrated into the anesthetic machine, or can be set up in the direct vicinity of the anesthetic machine (for example as so-called backpack) or some meters away from the anesthetic machine (for example in an adjacent room). The mass spectrometer is functionally connected to the anesthetic machine. The mass spectrometer can both monitor the anesthetic gas circulation and measure the gas fed in from the xenon recovery via two measurement channels simultaneously or alternately in short cycles.

A suitable mass spectrometer is a commercial apparatus supplied by Leybold AG (Cologne) with the designation Ecotec 500, which has a very compact design and already has a computer interface for transmitting the measured signal. This commercial apparatus can be employed without the elaborate apparatus peripherals hitherto customary with mass spectrometers and, when the sampling points are appropriately arranged, provides real-time measured data. The mass spectrometer is designed for the mass range from 1 to 100 atomic mass units. The restriction to this mass range makes a very compact design possible. Xenon has an atomic mass of 132 and cannot be determined directly with such an apparatus. The problem has been solved by doubly ionizing xenon (formation of $Xe^{2+}$) for the measurement.

The mass spectrometric measurements usually take place with clock-pulse rates of 1 measurement/second. The clock-pulse rate can also be chosen to be shorter or longer.

The monitoring of the recovered anesthetic gas-containing gas on entry into the anesthetic machine means that the recovery system is indirectly monitored from the anesthetic machine. Despite this indirect monitoring, there are no restrictions of any kind on the possibility of reacting to faults in the recovery operation, because the recovered gas is monitored exactly where it is used.

The computer normally present in an anesthetic machine furthermore makes it possible to use the analytical data for process control. Recovered anesthetic gas (for example xenon) and fresh anesthetic gas (from the gas cylinder, anesthetic gas source) can be automatically mixed via a valve control or flow regulator so that the anesthesia parameters preselected by the clinician are set up. Since the losses of xenon which regularly occur in the system must be compensated by adding fresh xenon, automatic control of the gas flows on the basis of the analytical results offers great advantages. In addition, the computer-assisted control of the mass spectrometer makes it possible continuously to document the gas-related anesthesia parameters and thus meets the requirement for continuous documentation of the progress of anesthesia.

It is furthermore possible to monitor and document, through a sampling point in the expiratory branch of the anesthesia circuit, which mixture of substances is fed from the anesthetic machine into the recovery.

If several anesthetic machines are coupled to a single recovery system, it is possible for each mass spectrometer independently of the others to interrupt the gas supply from the recovery in the event of faults or else to block the recovery system entirely. If, for reasons of simplicity, monitoring of the anesthesia circuit is dispensed with, the recovery can also be monitored by a single mass spectrometer which, depending on the number of connected anesthetic machines, is positioned between the recovery gas outlet and the point of branching to the anesthetic machines.

The described analytical configuration can also be used for anesthesia with conventional laughing gas. It is therefore possible to monitor the anesthesia circuit irrespective of the anesthetic gas chosen. This is particularly advantageous when modern anesthetic machines permit operation with xenon or laughing gas as selected. As a rule, no recovery unit is employed for anesthesia with laughing gas. If, for environmental protection or worker safety reasons, in future it becomes necessary for the outflowing laughing gas mixture to be destroyed on site, it will also be possible for such a disposal unit likewise to be monitored, controlled or documented with a mass spectrometer.

The choice of a mass spectrometer with reduced mass range and the described linkage into the system of anesthetic machine and recovery system entirely meet the functional requirements described above and, furthermore, can be implemented at costs which are distinctly below those to be expected with conventional mass spectrometers. This means that the described anesthesia system is reasonably priced and, furthermore, permits economic operation of xenon anesthesia.

BRIEF DESCRIPTION OF THE DRAWING

FIG. 1 shows a diagram of an anesthesia system in accordance with this invention.

DESCRIPTION OF THE PREFERRED EMBODIMENTS

FIG. 1 shows a diagram of an anesthesia system as example. The anesthesia system contains the gas supplies 1 (oxygen source), 2 (xenon source, "first supply"), 3 (xenon store, recovered xenon), an anesthetic machine 10, control unit 12 (computer or microprocessor), mass spectrometer 11 and monitor 13, and xenon recovery unit 15. The ventilation gas is mixed via valves 4 and 5 from oxygen from the oxygen source 1 and from xenon from the xenon source 2 and/or 3. Valves 4 and 5 are components of a so-called gas mixing box 17. The ventilation gas (inspired) is fed to the patient via line 22. The exhaled gas (expired) is fed to the xenon recovery 15 via line 24. Line 26 leads from the xenon recovery to the xenon store 3. Line 28 leads from the store 3 via valve 6 into line 20, which leads into the gas mixing box. Lines 22 (inspired), 24 (expired) and line 26 (xenon recovery outlet) are connected to the mass spectrometer via bypass lines 23, 25 and 27. Bypass lines 23, 25 and 27 each have a controllable valve 7, 8 and 9. Valves 4, 5, 6, 7, 8 and 9 are controlled by the control unit (computer). The control unit also undertakes the conventional control tasks. The mass spectrometer has one or more interfaces (computer interfaces) via which the measured signal, which represents the analytical result, is passed to the control unit. The control unit calculates the content of the gas components (for example oxygen, xenon, nitrogen) from the measured signal. The control unit is connected to the monitor 13 on which all the relevant information is shown. The xenon recovery 15 can take place, for example, as described in DE 44 11 533. Other xenon recovery methods can likewise be employed.

Anesthesia with the anesthesia system advantageously takes place in the following stages (example with xenon as anesthetic gas):
1. At the start of anesthesia, the patient is ventilated with a ventilation gas (oxygen/xenon mixture) and, during this, the composition of the inspired gas and expired gas is determined. In this initial phase, the lungs and airways of the patient are flushed. The expired gas contains nitrogen in this phase.
2. When the composition of the expired gas has stabilized and the nitrogen content has fallen to an acceptable level, the xenon recovery (determination of the starting point of the xenon recovery) is switched on.
3. The anesthesia reaches a stationary phase. The compositions of the inspired gas and expired gas are monitored. It is additionally possible to monitor the composition of the xenon gas from the xenon recovery.
4. The anesthesia is terminated by switching over from anesthetic gas to normal respiratory gas (air). The nitrogen content in the expired gas is of particular interest in this phase. As soon as the nitrogen content exceeds a limit (for example 5 percent by weight), the line with the expired gas is uncoupled from the xenon recovery.

Stages 1 to 4 require continuous monitoring of the composition of the inspired, expired and, advantageously, recovered gases. The monitoring takes place with one or more mass spectrometers. Controlled coupling of the mass spectrometer means that one mass spectrometer is sufficient.

It is advantageous for it to be possible to pick up the measured signal from the mass spectrometer directly on the machine in order to make a safety test possible independently of the control unit. When certain limits are reached, an alarm can be triggered. It is possible when recovered xenon is being fed in, and when the composition of the inspired gas shows an unacceptable difference from the desired value, to switch over to pure xenon from the reserve compressed gas cylinder (xenon source) (Switching over from xenon circulation to first and emergency supplies). It is advantageous for the actual value of the gas composition to be compared with a reference value from a reference gas mixture (for example from a pressure element) either directly in the mass spectrometer or in the control unit. The mass spectrometer can likewise be calibrated using a reference gas mixture from a pressure element. The mass spectrometer is advantageously also arranged so that an alarm is triggered if the pressure in the pressure element falls.

Automation of the anesthesia system may not only relate to computer-assisted control of valves but also comprise control of regulators for setting the gas flow rate. The design of a control for the gas flow rate is familiar to the skilled person.

Conditions for anesthesia with a low gas flow rate are described in the booklet by Jan Baum "Die Narkose mit niedrigem Frischgasfluß" [Anesthesia with a Low Fresh Gas Flow Rate], 2nd edition, Drägerwerk AG, Lübeck, 1994 (ISBN 3-921958-90-3), to which reference is made.

List of Reference Numbers

1 oxygen source
2 xenon source
3 xenon store
4, 5, 6, 7, 8, 9, valve, controlled 10 anesthetic machine
11 mass spectrometer
12 control unit (computer)
13 monitor
14 patient
15 xenon recovery
16 pump
17 gas mixing box
20, 21, 22, 23, 24, 25 gas line

What is claimed is:

1. In an anesthesia system having ventilation gas supply flow structure for supplying ventilation gas to a patient, exhaled gas flow structure for receiving exhaled gas from the patient and recycled anesthetic gas-containing gas flow structure for receiving recycled anaesthetic gas, the improvement being a mass spectrometer connected to the flow structures, the mass spectrometer measuring a content of at least one gas component in the ventilation exhaled or recycled anaesthetic gases, and the mass spectrometer controlling flow of the ventilation, exhaled or recycled anaesthetic gases through at least one of the flow structures in accordance with a measured value of the content.

2. Anesthesia system as claimed in claim 1 including structure for the mass spectrometer for simultaneous quantitative measurement of oxygen, anesthetic gas and nitrogen.

3. Anesthesia system as claimed in claim 2, wherein the mass spectrometer controls a safety unit.

4. Anesthesia system as claimed in claim 3, wherein the mass spectrometer is connected via one or more capillaries to one or more measuring points.

5. Anesthesia system as claimed in claim 4, wherein the mass spectrometer is connected via one or more capillaries to the measuring points, and the length of the capillaries is in the range from 1 to 10 meters.

6. Anesthesia system as claimed in claim 5, wherein the mass spectrometer is connected via one or more capillaries to the measuring points, and the capillaries consist of plastic, metal or glass.

7. Anesthesia system as claimed in claim 6, wherein the mass spectrometer is integrated into an anesthetic machine, and the mass spectrometer is attached as backpack to the anesthetic machine.

8. Anesthesia system as claimed in claim 6, wherein the mass spectrometer is integrated into an anesthetic machine or is spatially separated from the machine.

9. Anesthesia system as claimed in claim 1, wherein xenon is employed as anesthetic gas, and the recovery of xenon from the exhaled gas is monitored or controlled by the mass spectrometer.

10. Anesthesia system as claimed in claim 9, wherein the mass spectrometer makes continuous measurements for several measuring points alternately.

11. Anesthesia system as claimed in claim 1, wherein the mass spectrometer controls a safety unit.

12. Anesthesia system as claimed in claim 1, wherein the mass spectrometer is connected via one or more capillaries to one or more measuring points.

13. Anesthesia system as claimed in claim 1, wherein the mass spectrometer is connected via one or more capillaries to measuring points, and the length of the capillaries is in the range from 1 to 10 meters.

14. Anesthesia system as claimed in claim 1, wherein the mass spectrometer is connected via one or more capillaries to measuring points, and the capillaries consist of plastic, metal or glass.

15. Anesthesia system as claimed in claim 1, wherein the mass spectrometer is integrated into an anesthetic machine, and the mass spectrometer is attached as backpack to the anesthetic machine.

16. Anesthesia system as claimed in claim 1, wherein xenon is employed as anesthetic gas, and the recovery of xenon from the exhaled gas is monitored or controlled by the mass spectrometer.

17. Anesthesia system as claimed in claim 1, wherein the mass spectrometer makes continuous measurements for several measuring points alternately.

* * * * *